(12) United States Patent
Mann et al.

(10) Patent No.: US 8,264,694 B2
(45) Date of Patent: Sep. 11, 2012

(54) QUANTITATIVE PHASE-CONTRAST AND EXCITATION-EMISSION SYSTEMS

(75) Inventors: Christopher J. Mann, Knoxville, TN (US); Philip R. Bingham, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 113 days.

(21) Appl. No.: 12/405,089

(22) Filed: Mar. 16, 2009

(65) Prior Publication Data
US 2010/0231896 A1    Sep. 16, 2010

(51) Int. Cl.
*G01B 11/02* (2006.01)
(52) U.S. Cl. ...................................... 356/512
(58) Field of Classification Search .............. 356/73, 356/456, 489, 496, 511, 503, 512
See application file for complete search history.

(56) References Cited

U.S. PATENT DOCUMENTS

| | | | |
|---|---|---|---|
| 4,453,827 A * | 6/1984 | Taboada | 356/520 |
| 4,701,006 A | 10/1987 | Perlmutter | |
| 5,418,797 A * | 5/1995 | Bashkansky et al. | 372/3 |
| 6,002,480 A * | 12/1999 | Izatt et al. | 356/479 |
| RE36,529 E * | 1/2000 | Lewis et al. | 356/456 |
| 6,760,134 B1 | 7/2004 | Schilling et al. | |
| 6,809,814 B2 * | 10/2004 | Xie et al. | 356/301 |
| 6,809,845 B1 | 10/2004 | Kim et al. | |
| 6,943,924 B2 | 9/2005 | Marquet et al. | |
| 7,127,109 B1 | 10/2006 | Kim | |
| 7,312,875 B2 | 12/2007 | Hanson et al. | |
| 7,364,296 B2 | 4/2008 | Miller et al. | |
| 7,978,336 B2 * | 7/2011 | Mann et al. | 356/485 |
| 2006/0132799 A1 * | 6/2006 | Dubois et al. | 356/512 |
| 2008/0287929 A1 * | 11/2008 | Holliday et al. | 606/5 |
| 2008/0304046 A1 * | 12/2008 | Lee et al. | 356/51 |

OTHER PUBLICATIONS

Goodman, J. W., *Introduction to Fourier Optics*. 2ed. McGraw-Hill, New York, New York, Copyright 1996, 456 pages.

Schnars, U. et al., "Direct recording of holograms by a CCD target and numerical reconstruction," *Applied Optics*, vol. 33, No. 2, 1994, pp. 179-181.

Török, P. et al., *Optical Imaging and Microscopy: Techniques and Advanced Systems*, Springer, Berlin, Germany, Copyright 2003, 405 pages.

Warnasooriya, N. et al., "LED-based multi-wavelength phase imaging interference microscopy," *Optics Express*, vol. 15, No. 15, 2007, pp. 9239-9247.

Yamauchi, T., "Low-coherent quantitative phase microscope for nanometer-scale measurement of living cells morphology," *Optics Express*, vol. 16, No. 16, 2008, pp. 12227-12238.

(Continued)

*Primary Examiner* — Tarifur Chowdhury
*Assistant Examiner* — Jonathan Hansen
(74) *Attorney, Agent, or Firm* — Brinks Hofer Gilson & Lione

(57) ABSTRACT

An optical system includes an optical interferometer that generates interference phenomena between optical waves to measure multiple distances, thicknesses, and indices of refraction of a sample. An excitation-emission device allows an electromagnetic excitation and emission to pass through an objective in optical communication with the sample. An electromagnetic detector receives the output of the optical interferometer and the excitation-emission device to render a magnified image of the sample. A digital delay generator synchronizes the optical interferometer and excitation-emission device to operate in substantially unison to generate a noninvasive depth of field of the portion of the sample that corrects a plurality of optical aberrations in real-time.

21 Claims, 6 Drawing Sheets

OTHER PUBLICATIONS

Yu, L. et al., "Improved tomographic imaging of wavelength scanning digital holographic microscopy by use of digital spectral shaping," *Optics Express*, vol. 15, No. 3, 2007, pp. 878-886.

Yu, L. et al., "Wavelength scanning digital interference holography for variable tomographic scanning," *Optics Express*, vol. 13, No. 15, 2005, pp. 5621-5627.

Yamaguchi, Ichirou et al.; "Phase-shifting color digital holography";Optics Letters, vol. 27, No. 13; Jul. 1, 2002; pp. 1108-1110.

Bachim, B. L. et al., "Microinterferometric optical phase tomography for measuring small, asymmetric refractive-index differences in the profiles of optical fibers and fiber devices," *Applied Optics*, vol. 44, No. 3, 2005, pp. 316-327.

Beuthan, J. et al., "The spatial variation of the refractive index in biological cells," *Phys. Med. Biol.*, vol. 41, 1996, pp. 369-382.

Charrière, F. et al., "Living specimen tomography by digital holographic microscopy: morphometry of testate amoeba," *Optics Express*, vol. 14, No. 16, 2006, pp. 7005-7013.

Choi, W. et al., "Extended depth of focus in tomographic phase microscopy using a propogation algorithm," *Optics Letters*, vol. 33, No. 2, 2008, pp. 171-173.

Cuche, E. et al., "Digital holography for quantitative phase-contrast imaging," *Optics Letters*, vol. 24, No. 5, 1999, pp. 291-293.

Ferraro, P. et al., "Quantitative phase-contrast microscopy by a lateral shear approach to digital holographic image reconstruction," *Optics Letters*, vol. 31, No. 10, 2006, pp. 1405-1407.

Ferraro, P. et al., "Quantitative Phase Microscopy of microstructures with extended measurement range and correction of chromatic aberrations by multiwavelength digital holography," *Optics Express*, vol. 15, No. 22, 2007, pp. 14591-14600.

Goodman, J. W. et al., "Digital Image Formation form Electronically Detected Holograms," *Applied Physics Letters*, vol. 11, No. 3, 1967, pp. 77-79.

Grilli, S. et al., "Whole optical wavefields reconstruction by Digital Holography," *Optics Express*, vol. 9, No. 6, 2001, pp. 294-302.

Huntley, J. M. et al., "Temporal phase-unwrapping algorithm for automated interferogram analysis," *Applied Optics*, vol. 32, No. 17, 1993, pp. 3047-3052.

Iwai, H. et al., "Quantitative phase imaging using actively stabilized phase-shifting low-coherence interferometry," *Optics Letters*, vol. 29, No. 20, 2004, pp. 2399-2401.

Kim, M. K. et al., Chapter 2, "Digital Holography and Multi-Wavelength Interference Techniques," *Digital Holography and Three-Dimensional Display: Principles and Applications*, Springer, New York, New York, Copyright 2006, pp. 51-72.

Kühn, J. et al., "Real-time dual-wavelength digital holographic microscopy with a single hologram acquisition," *Optics Express*, vol. 15, No. 12, 2007, pp. 7231-7242.

Lo, C. F., "Surface normal guided method for two-dimensional phase unwrapping," *Optik*, vol. 113, No. 10, 2002, pp. 439-447.

Lue, N. et al., "Quantitative phase imaging of live cells using fast Fourier phase microscopy," *Applied Optics*, vol. 46, No. 10, 2007, pp. 1836-1842.

Mann, C. J. et al., "High-resolution quantitative phase-contrast microscopy by digital holography," *Optics Express*, vol. 13, No. 22, 2005, pp. 8693-8698.

Mann, C. J. et al., "Movies of cellular and sub-cellular motion by digital holographic microscopy," *BioMedical Engineering OnLine*, vol. 5, 2006, pp. 1-10.

Mann, C. J. et al., "Quantitative phase imaging by three-wavelength digital holography," *Optics Express*, vol. 16, No. 13, 2008, pp. 9753-9764.

Park, Y. et al., "Diffraction phase and fluorescence microscopy," *Optics Express*, vol. 14, No. 18, pp. 8263-8268, Sep. 4, 2006.

\* cited by examiner

QUANTITATIVE PHASE-CONTRAST AND EXCITATION-EMISSION SYSTEMS

RELATED APPLICATION

This application is related to U.S. application Ser. No. 12/405,063 filed on Mar. 16, 2009, entitled "Quantitative Phase-Imaging Systems," and U.S. application Ser. No. 12/381,758 filed on Mar. 16, 2009, entitled "Three Wavelength Quantitative Imaging Systems," which are incorporated by reference.

BACKGROUND OF THE INVENTION

1. Technical Field

This disclosure relates to optical systems and particularly to systems that apply transmissive and reflective magnifications.

2. Related Art

Biological processes and structures of transparent objects are of interest in the life science fields. To quantify or even observe these processes is limited by some bright-field microscopes. Some microscopes have small depths of focus at high lateral magnifications. Others have limited capability to effectively observe transparent samples such as living biological cells which exhibit very little intensity contrast.

SUMMARY

An optical system images in transmissive and reflective modes. The system includes an optical interferometer that generates interference phenomena between optical waves to measure multiple distances, thicknesses, and indices of refraction of a sample. An excitation-emission device allows an electromagnetic excitation and emission to pass through an objective in optical communication with the sample. An electromagnetic detector receives the output of the optical interferometer and the excitation-emission device to render a magnified image of the sample in real-time. A digital delay generator synchronizes the optical interferometer and excitation-emission device to operate substantially in unison to generate a noninvasive depth of field of the portion of the sample that corrects a plurality of optical aberrations in real-time.

Other systems, methods, features, and advantages, will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
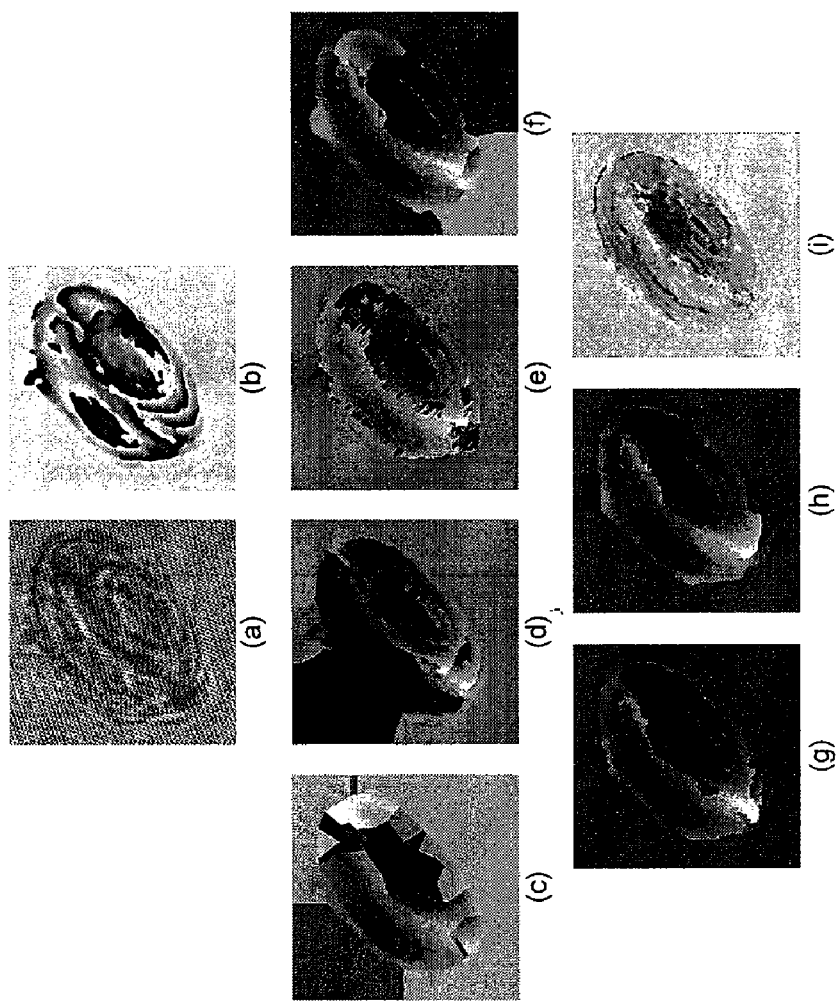
FIG. 1 is a plurality of images of a pollen grain.

Quantifying optical path length changes may detect refractive indexes or optical thickness variations with a vertical resolution of a few nanometers. The quantification may be used to investigate morphological variations associated with dynamic biological processes, such as drug delivery, disease progression, and/or other pathological occurrences.

Unlike some phase-shifting systems, an optical system may include one or more digital optical interferometers that may not require multiple image acquisitions or phase modulations. The data or information in a complete volume may be recorded in a single digital image within a local or a remote memory or database that facilitates real-time imaging and viewing (e.g., through a display) locally or at a remote site. The speed of the image capture may depend on the frame rate of capture of an interfaced recording device or latency in which the data is stored or written into the local and/or remote memory. The magnification may differ from some phase-shifting techniques, in which the speed of image capture may depend on the speed at which the phase-shifting device may be adjusted.

The intensity and phase information of the optical system that includes a digital optical interferometer device may be simultaneously (or nearly simultaneously) reconstructed from a stored or recorded complex wave-front in high-speed (e.g., at the same rate the data is received), allowing some optical systems to function as a bright-field and quantitative phase-contrast microscope in real-time. The information in the phase image may be determined by a thickness/refractive index variations (in some optical systems exclusively) that allow living biological cells to be observed without staining. The optical interferometer device may be numerically focused to emulate focus controls of other magnifying devices but with higher resolution. Because focusing may be adjusted in a reconstruction process, a digital optical interferometer device may be free of the limitations of a mechanical focused system. This feature may allow the optical system to monitor a sample's dynamics irrespective of depth variations.

To specify detailed information that identifies individual structures, the optical systems may include an excitation-emission device (or epi-fluorescence devices in alternate optical systems). The excitation-emission device may generate emissions (or florescence in some optical systems) by reflection (rather than transmitted light) to magnify the functional details of a sample. The excitation-emission magnification may occur on a discrete schedule (e.g., enabling the excitation-emission and optical interferometer devices in sequence or series), interactively, in real time and/or continuously with one or more digital optical interferometer magnifications or devices.

The correlation between the transmissive and reflective magnifications may be processed to analyze the relationship between cellular structures and function through a local or remote signal processor. To obtain quantitative phase data, some optical systems include one or more multiple-wavelength digital optical interferometers (or holographic devices in some alternate systems). Multiple wavelengths may provide a deterministic method to obtain phase data beyond a characteristic ambiguity limit. Some optical systems eliminate time consuming phase unwrapping algorithms or processes that may be prone to errors. By performing imaging in a transmissive and a reflective mode, the optical system may obtain quantitative phase data both deterministically and with high speed. The optical system may capture a large depth of field in a single image (e.g., a single shot), provide numerical focusing that renders distinctness and image clarity, and the correction of optical aberrations in real-time with a non-invasive system.

In some optical systems increasing the phase range (optical phase unwrapping) may be implemented through two or more wavelengths. The combination of phase images of two different wavelengths $\lambda_1$ and $\lambda_2$ may render another phase image having an effective wavelength (or synthetic wavelength) described by equation 1.

$$\Lambda_{12}=\lambda_1\lambda_2/|\lambda_1-\lambda_2|. \tag{1}$$

At an effective wavelength, the measured phase is measured longer than either of the two probing wavelengths. This approach may eliminate the problems of mathematical phase unwrapping algorithms. The process is deterministic, does not have problems with certain mapping or image topologies, and may be processed at times that may measure about a fraction of a second. FIG. 1 illustrates a phase-unwrapping comparison between some software based unwrapping algorithms and a two wavelength optical approach on a wrapped pollen grain image. The two wavelength image displays a greater accuracy and recovery of the complete phase range than the illustrated unwrapped images which include many inconsistencies and areas where it has completely failed to determine the wrap points (illustrated in black). A comparison between the application of phase unwrapping algorithms and exemplary synthetic wavelength processing on a phase-wrapped pollen grain image are shown through the series of drawings in which (a) is an exemplary digital hologram of pollen grain (b) is a corresponding reconstructed wrapped phase image, (c) is a corresponding phase unwrapped images by a Goldstein's algorithm; (d) is a corresponding phase unwrapped images by a Minimum $L^P$ Norm process; (e) is a corresponding phase unwrapped images by a Mask Cut algorithm; (f) is a corresponding phase unwrapped images by a Full Multi-Grid (FMG) process; (g) is a corresponding phase unwrapped images by a Quality Mapped process; (h) is a corresponding phase unwrapped images by a Flynn's Minimum Discontinuity process; and (i) is a corresponding image rendered by a two-wavelength optical system or process. The optical system that rendered (i) applied a synthetic wavelength of $\Lambda_{12}$=9.6 µm. Software-based algorithm time for the single image renderings of images (b) through (h) had a processing time that ranged between 27 to 310 seconds. The two-wavelength single image processing time comprised about 26 ms.

To obtain a longer measurement range, the two wavelength values $\lambda_1$ and $\lambda_2$ (from equation 1) may be selected close together. When the difference between the two images is taken from wavelengths that are far apart, some synthetic wavelengths, $\Lambda_{12}$, may become noisy due to amplification error. This effect may be minimized or substantially overcome in alternate optical systems that include three or more wavelength digital optical interferometer or holographic devices. These devices may use a hierarchical synthetic-wavelength reduction process. The use of three or more wavelength digital optical interferometers or holographic devices may facilitate longer range measurements without increasing the phase noise. As the multiple-wavelength wave-front may be captured in real-time, the alternate system may make direct, long-range shape measurements of dynamically moving samples in high resolution in real-time or at an improved speed.

Figure 2:
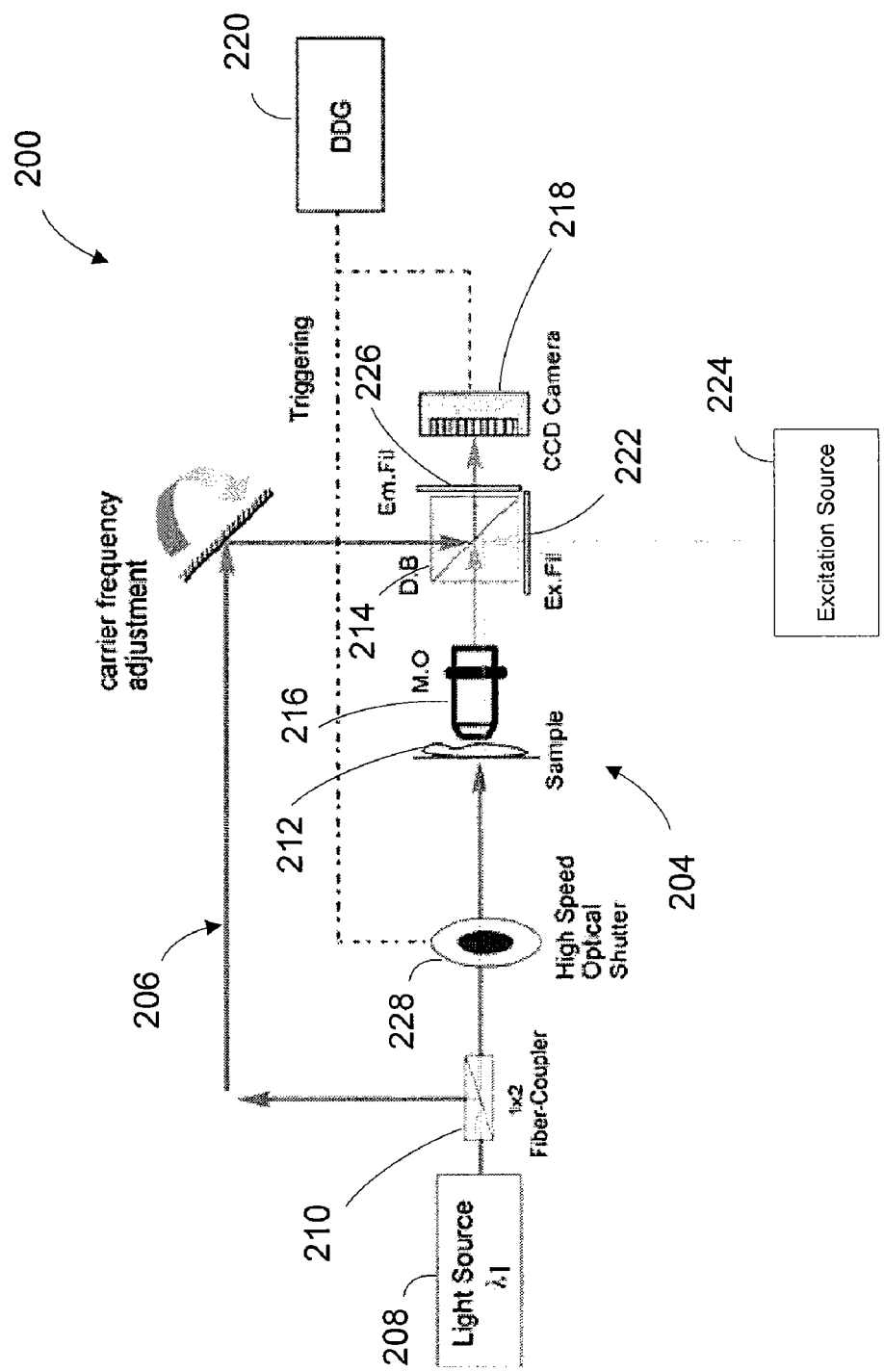
FIG. 2 is a single wavelength optical interferometer and excitation-emission device.

FIG. 2 is a single wavelength optical system 200 (that includes an interferometer) that may perform imaging in a transmissive and/or reflective mode. An object and reference beams 204 and 206 are created along two separate and well-defined optical paths using a fiber optic delivery system. The object beam 204 and reference beam 206 originate from a light source 208 that sources an electromagnetic spectrum in a visible or an invisible range to a common input of a 1×2 fiber optic coupler 210. An optical shutter 228 (e.g., a high speed optical shutter) movable or rotatable through the object path controls the frequency and duration of exposure of the sample 212 to the object beam 204 by rotating one or more lenses through the object path. While positioned between the fiber optic coupler 210 and the sample 212 in FIG. 2, in alternate systems the optical shutter 228 is positioned between a beam splitter 214 (e.g., filter cube) and the microscope objective 216. The optical shutter 228 may be synchronized to a Charge Coupled Device (CCD) such as a monochrome CCD camera 218 through a Digital Delay Generator (DDG) 220 or controller. In some optical systems, the DDG 220 or controller accesses or communicates with a non-volatile memory (e.g., flash memory) to execute programmable sequences and delays. This synchronization allows the quantitative phase and emissions (e.g., fluorescence information) to be obtained synchronously or concurrently.

An angle is created between the object and the reference beams 204 and 206 for off-axis optical interferometer rendering (e.g., holography) by tilting the combination of a reflecting surface (or mirror) in the reference beam 206 path and a beam splitter 214 (e.g., like the dichroic beam splitter shown in FIG. 2). The tilt provides a frequency modulation in the interference between the object and the reference beams 204 and 206 which creates a separation of a respective optical interferometers (or holographic) and DC terms in a Fourier space. The CCD (e.g., CCD camera) may record the digital optical interferometer output (or hologram) before it is digitally transferred to a local or remote controller through a wireless or tangible link. The quantitative amplitude and phase of the complex wave-front may then be extracted and processed.

To excite the excitation objects within (or florescence within) the species in the sample, a high intensity light source 224 such as a mercury lamp, for example, may illuminate the sample. Optics within the excitation-emission device (or epi-fluorescence device) separate the illumination (or excitation) light from the emission that emanates from the sample 212 that passes through the microscope objective 216. To select the proper excitation wavelength, an excitation filter 222 is disposed in the excitation path between the excitation light source 224 and the beam splitter 214. A wavelength selective device, such as an emission filter 226 selects the emission wavelengths of the electromagnetic spectrum emitted from the sample 212. The wavelength selective device may be placed between the beam splitter 214 and the CCD 218 to select the emission wavelength and eliminate nearly any or substantially all of the wavelengths used for excitation.

Figure 3:
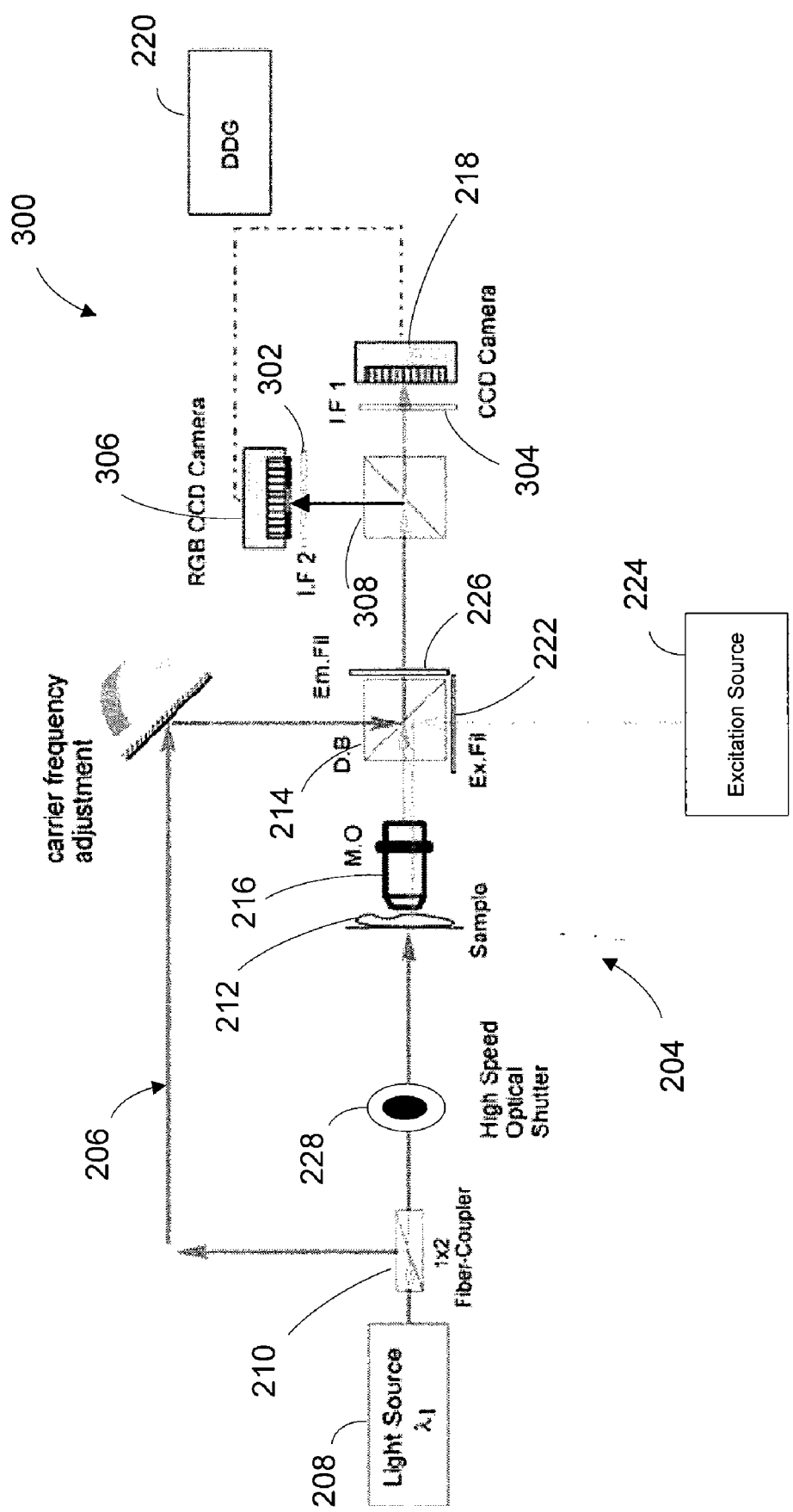
FIG. 3 is a second single wavelength optical interferometer and excitation-emission device.

FIG. 3 is another alternative single wavelength optical system. In this system separation of the phase and emission (for explanation rather than limiting purposes, a fluorescence emission is described) information occurs through interference filters 302 and 304 and multiple image capturing devices. Multiple CCD sensors that acquire different color components like device optically aligned with RGB filters or an RGB CCD camera 306 that enables fluorescence information (or other emissions in other applications) to be captured in each channel of the camera in real-time and at a high rate of speed. A CCD camera such as the monochrome CCD 218 of FIG. 3 may provide high resolution images and improved spectral response over longer wavelengths (e.g., into the infrared range). In some applications, a monochrome CCD camera may capture biological imaging. When subject to multiple fluorescent excitations that create many emissions, an RGB camera may enables the fluorescence information to be captured in each channel of the camera in real-time and at a high rate of speed.

In FIG. 3 optical filters such as interference filters 302 and 304 may pass optical frequencies within a certain frequency range (band) but substantially block or attenuate signals above and/or below a band. The interference filters 302 and 304 may be disposed between filter cube 308 (e.g., a dichroic surface or mirror that includes an adjustment device to change the inclination of the surface without directly handling the surface or filters) and the inputs of the RGB CCD 306 and a monochrome CCD camera 218 so that only (or substantially most of) the respective interference phenomena (or holographic phenomena) or fluorescence information or data is passed to the respective cameras. The high speed optical shutter 228 between the fiber optical coupler 210 and the sample 212 or between the microscope objective 216 and the beam splitter 214 may replace or supplement the interference filters 320 and 304 in alternate optical systems.

Figure 4:
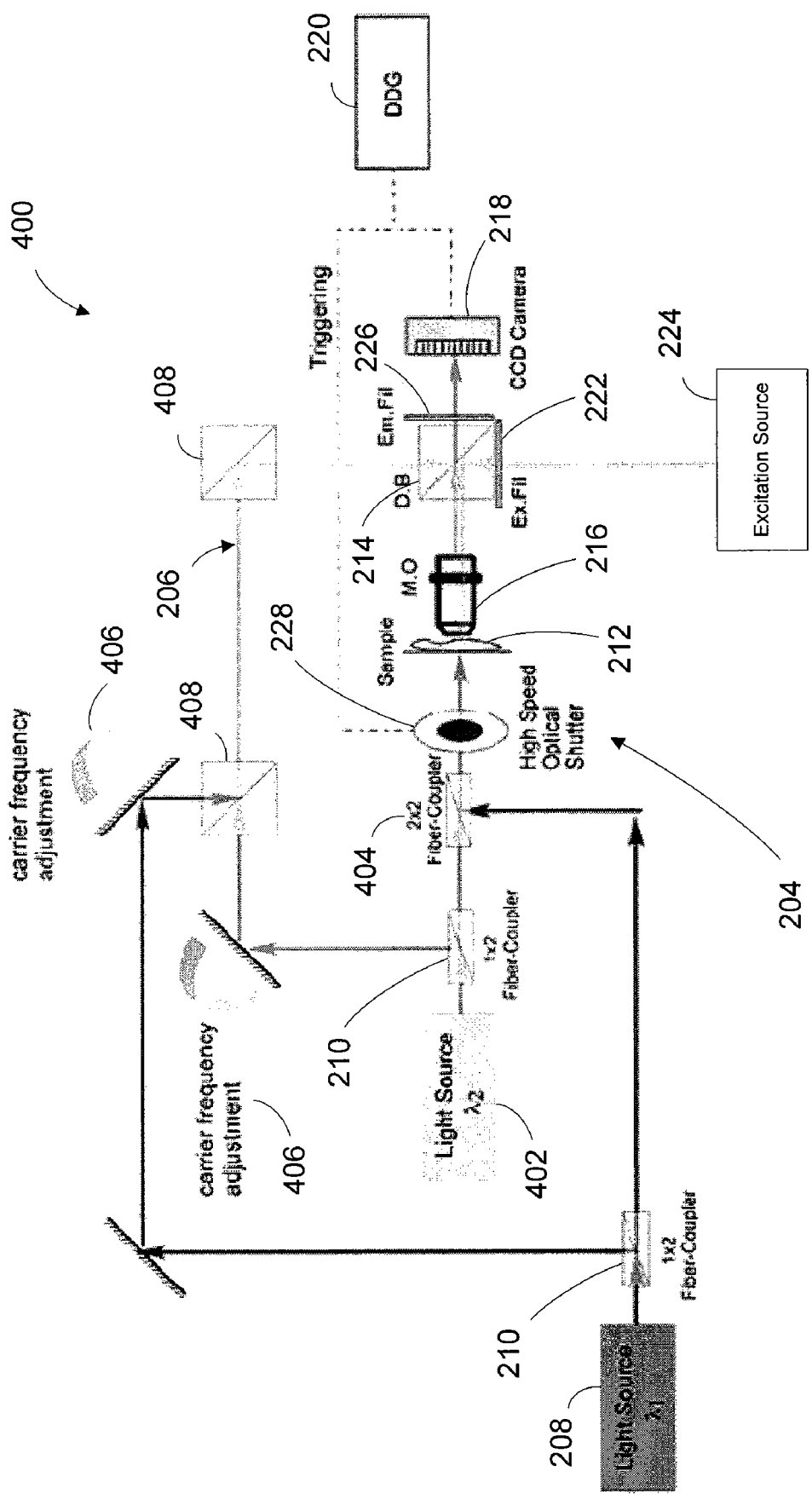
FIG. 4 is a multiple wavelength optical interferometer and excitation-emission device.

FIG. 4 shows a two wavelength optical system 400 that includes two interferometers in an achromatic arrangement that brings two wavelengths emitted from two light sources into one imaging optical system. The reference beams 206 of each holographic device or interferometer may be adjusted so that the two holograms (or two interference phenomena) may be recorded or written to memory through a single digital image through different sets of spatial frequencies. The optical system 400 may capture multiple-wavelengths of a complex wave-front in real-time.

In the arrangement of FIG. 4, the reference beams originate from two (e.g., multiple) separate light sources 208 and 402 that have electromagnetic spectrums in the visible or invisible electromagnetic range. Fiber optic couplers 210 having three or more fiber optic ends split the input fiber optic light into two or more parts to the outputs (e.g., the object path and the reference path) at a predetermined ratio. The fiber optic coupler 210 may interface a single mode fiber optic cable and may comprise a single window. A single window may have a single wavelength with a narrow wavelength window. A multiple window fiber optic coupler (not shown) may support two or more wavelengths in alternate systems with a wide wavelength window for each input.

A fiber optic coupler 404 combines the object beams in the object path. Tilting reflective surfaces (or mirrors) 406 in the reference paths separate the wavelength frequencies in the Fourier domain. The individual heterodyning established by these surfaces prevents overlap or shifts the interference frequency in Fourier space before the reference beams are combined and directed by the filter cubes 408 to the beam splitter 214.

An optical shutter 228 (e.g., a high speed optical shutter) movable or rotatable through the object path controls the frequency and duration of exposure of the sample 212 to the composite object beam 204 by rotating one or more lenses through the object beam channel. While positioned between the fiber optic coupler 404 and the sample 212 in FIG. 4, in alternate systems the optical shutter 228 is positioned between the beam splitter 214 and the microscope objective 216. The optical shutter 228 may be synchronized to a CCD such as a monochrome CCD camera 218 using a DDG 220 or controller. This synchronization allows the quantitative phase and fluorescence information to be obtained synchronously or concurrently in real-time.

When the interference phenomena or holograms have been captured through a CCD device or camera 218, they may be transmitted through a parallel or serial interface (e.g. an IEEE 1394b) and a wireless or tangible medium to a remote or local processor or signal processor. Numerical band-pass filters (devices or programs) may process the separate interference or holographic terms originating from the multiple wavelengths, from which the interference or holographic phase images may be reconstructed. Through the numerical focusing of the digital interferometer or holographic devices, the reconstructed images at each wavelength may be focused to enable an exact (or nearly exact superposition) of the sample 212. When three different lights sources (or more) are used in an alternate optical system (e.g., three or more optical interferometers), the alternate optical system may further enhance the measurement capability, allowing for long range phase imaging while maintaining the high-precision of the measurement.

In some optical systems, communication may occur through a wireless protocol. The communication protocol may provide an interoperable communication link with CCD and sensors, DDG devices 220, external applications, processors and/or remote sites. In some systems, the wireless links provides connectivity when the wireless network or a wireless service provider indicates a channel capacity or excess channel capacity to transfer some or all of the desired data to a destination. A CCD device may push desired data to a destination and may keep a connection open to allow the CCD device, sensors, DDG device 220, controllers, and/or etc. (CCD et al.), to continue to send desired data or respond to external requests (e.g., queries) as a sample is monitored (e.g., in real-time). A CCD et al. may pull data from a site in real-time too through a persistent or non-persistent connection.

Each of the systems described (or to be described) may include a wireless transceiver compliant with a cellular or wireless protocol, a wireless or cellular telephone, a radio, a satellite, or other wireless communication system that may link the CCD et al to a privately accessible or publicly accessible distributed network or directly to an intermediate surrogate or central operations center. The communication link may comprise Mobile-FI or a low-cost, always-on, mobile broadband wireless network that may have IP (Internet Protocol) roaming & handoff (at more than about 1 Mbit/s), MAC and PHY with IP and adaptive antennas, full mobility or substantial mobility up to vehicle speeds of about 88.7-162 km/h or higher (e.g., 250 km/h), operate in frequency bands (below 3.5 GHz), and/or utilize a packet architecture and have a low latency.

In some applications, the optical system may be Ultra-wideband compliant and may transmit information by generating radio energy at specific time instants and occupying large bandwidth, thus enabling a pulse-position or time-modulation communications. This protocol may be different from other wireless protocols that transmit information by varying the power level, frequency, and/or phase of a sinusoidal wave.

In other applications, the optical device may be complaint with WiMax or IEEE 802.16a or may have a frequency band within a range of about 2 to about 11 GHz, a range of about 31 miles, and a data transfer rate of about 70 Mbps. In other applications, the mobile monitoring device 100 may be compliant with a Wi-Fi protocols or multiple protocols or subsets (e.g., ZigBee, High Speed Packet Access (e.g., High Speed Downlink Packet Access and/or High Speed Uplink Packet Access), Bluetooth, Mobile-Fi, Ultrawideband, Wi-Fi, WiMax, mobile WiMax, cellular, satellite, etc., referred to as the transceiver protocols) that may be automatically detected and selected (through a handshaking, for example, that may automatically determine the source type of the transmission e.g., by a query for example, and may attempt to match it) and may enable this automatic access through one or more communication nodes.

To excite the florescent species in the sample of FIG. 4, a high intensity light source 224 such as a mercury lamp, for example, may illuminate the sample. Optics within an exemplary epi-fluorescence (or excitation-emission) device separate the illumination (or excitation) light from the (florescence) emission that emanates from the sample that passes through the microscope objective 216. To select the proper excitation wavelength, an excitation filter 222 is disposed in the excitation path between the high intensity light source 224 and the beam splitter 214. A wavelength selective device, such as an emission filter 226 selects the emission wavelengths of light emitted from the sample 212. The wavelength selective device may be placed between the beam splitter 214 and the CCD 218 to select the emission wavelength and eliminate nearly any or substantially all of the wavelengths used for excitation. The (fluorescence) data is separated from the interferometer (or holographic) data by the high-speed shutter 228 (may be driven by a closed loop servomotor monitored by a rotary encoder) and the DDG 220.

In each of the systems described (or to be described), an optional visual output device or display that may interface the local or remote memory, a remote or local processor, the CCD et al., etc. The display may support a graphical user interface that may allow an operator to enter point of interest identifiers (through icons, menus, dialog boxes, etc. selected through absolute and/or relative pointing devices) so that recorded characteristics may be associated with an image or a map (e.g., a topological map or simplified map that lacks some details or a topographic map that may show many details through contour lines, models, or other visual representations, or etc., for example). Some graphical user interfaces interface a touch screen that recognizes location and the intensity of touch (or simultaneous touches) on its surface by an operator or input device.

Some or all of optical systems may communicate with an optional visual output that may comprise a Light Emitting Diode display (LED), a Liquid Crystal display (LCD), or a remote controller (e.g., a computer screen, portable computer, a tablet computer, a personal digital device, and/or other displays) wirelessly or tangibly linked to the optical system. In some systems, the display may render real-time or delayed audio, visual, and/or tactile representations when a condition is detected, completed, is measured, or a programmed event occurs, etc.

Figure 5:
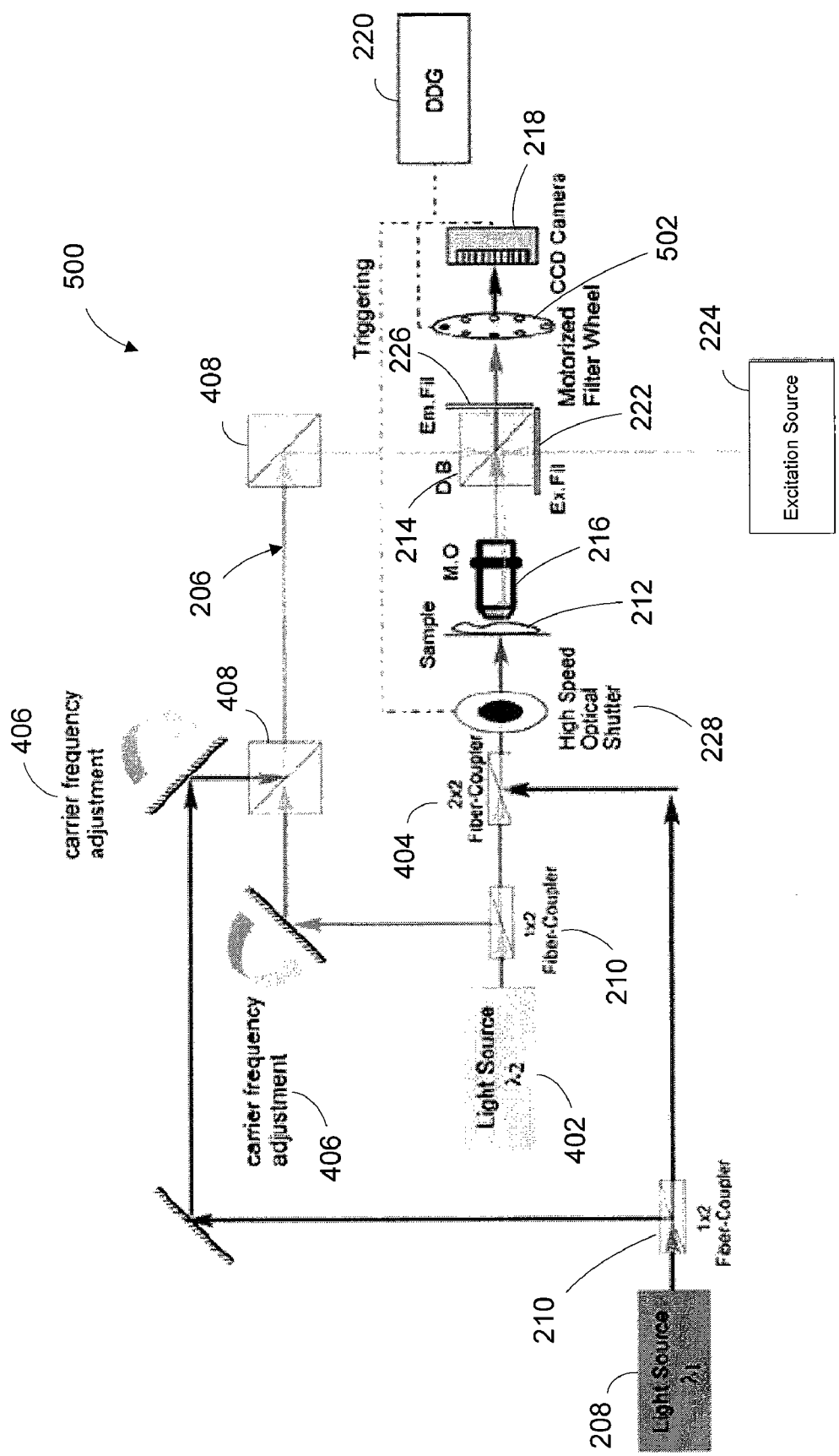
FIG. 5 is a second multiple wavelength optical interferometer and excitation-emission device.

FIG. 5 shows an alternate two wavelength optical system 500 that includes two interferometers an achromatic arrangement that brings two wavelengths emitted from two different light sources into one imaging optical system. The reference beams of each interferometer or holographic device may be adjusted so that the two interference phenomena or holograms may be recorded or written to memory through a single digital image through different sets of spatial frequencies. The optical system 500 may capture multiple-wavelengths of a complex wave-front in real-time.

In FIG. 5 a processor (or computer) controlled optical filter wheel 502 functions with the structure of FIG. 4. The optical filter wheel 502 is disposed between the beam splitter 214 and the monochrome CCD camera 218. In some systems the optical filter wheel 502 may comprise a highly accurate (direct or chain driven) system that may include no internal lights to ensure images are not compromised. A closed-loop servomotor may provide high speeds (e.g., in the low milliseconds between adjacent positions) and a low vibration operation. In some optical systems, a high-resolution rotary encoder may be optically linked to the optical filter wheel 502 (and/or mechanically linked to the servomotor) and may transmit positional feedback data to the DDG 220 or alternate optical system controller. A filter wheel controller or processor may utilize or access a non-volatile flash memory to read and store programmable filter sequences and delays. Motion may be triggered by an input pulse, and some filter wheel controllers will output a sync pulse to the DDG 220 or alternate optical system controller upon arrival or positioning at the commanded filter position. The optical filter wheel 502 may allow each wavelength band of the emission to be captured in succession by the monochrome CCD camera 218 allowing different components of a salient emission (or fluorescence) to be imaged in real-time.

Figure 6:
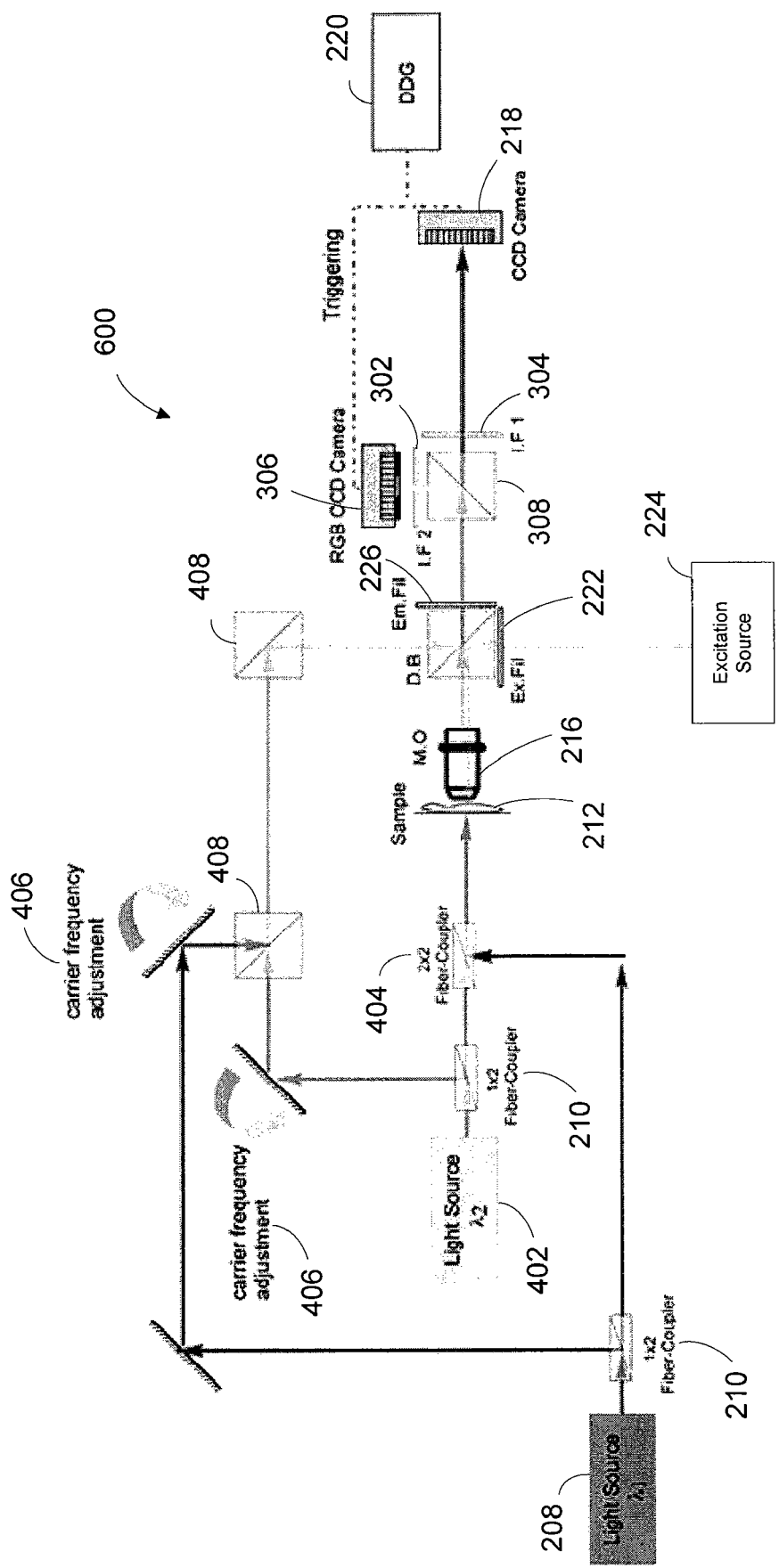
FIG. 6 is a third multiple wavelength optical interferometer and excitation-emission device.

In FIG. 6 RGB filters in communication with a recording device or an RGB CCD camera 306 that enables fluorescence information to be captured in each channel of the camera in real-time is added to the structure of FIG. 4. In FIG. 5 optical filters such as interference filters 302 and 304 are also added. The filters 302 and 304 may pass optical frequencies within a certain frequency range (band) but block or substantially attenuate signals above and/or below a band. The interference filters 302 and 304 may be disposed between a filter cube 308 and the inputs of the RGB CCD 306 and monochrome CCD camera 218 so that only (or substantially most of) the respective interference phenomena (or holographic) or emission (or fluorescence) information or data is passed to the respective cameras 218 and 306. While not included in the optical system of FIG. 5 to minimize noise and vibrations, a high speed optical shutter 228 disposed between the fiber optical coupler 404 and the sample 212 or between the microscope objective 216 and the beam splitter 214 may replace or supplement the interference filters 302 and 304 in alternate optical systems.

Other alternate systems and methods may include combinations of some or all of the structure and functions described above or shown in one or more or each of the figures. These systems or methods are formed from any combination of structure and function described or illustrated within the figures.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. An optical system comprising:
a plurality of optical interferometers configured to:
split light emitted from a plurality of light sources into first optical waves and second optical waves,
combine the first optical waves into a first combined optical wave that is transmitted through a sample and combine the second optical waves into a second combined optical wave to serve as a reference wave, and
generate an interference phenomena between the first combined optical wave that is transmitted through the sample and the second combined optical wave to measure a plurality of distances, a plurality of thicknesses, and a plurality of indices of refraction of at least a portion of the sample, an objective in optical communication with the sample, the objective configured to:
  receive the first combined optical wave after the first combined optical wave is transmitted through the sample;
  transmit an electromagnetic excitation to the sample, the electromagnetic excitation being transmitted to the sample for generation of emissions by the sample when the sample is subjected to the electromagnetic excitation; and
  receive the emissions generated by the sample;
an excitation-emission device configured to transmit the electromagnetic excitation to the objective;
an electromagnetic detector that receives at least one output of the plurality of optical interferometers and an output of the excitation-emission device to render a magnified image of at least a portion of the sample;
a digital delay generator that synchronizes at least one of the plurality of optical interferometers and the excitation emission device to operate in substantially unison to generate a noninvasive depth of field of the portion of the sample that corrects a plurality of optical aberrations in real-time; and
a display that renders a magnified image of the at least portion of the sample in realtime.

2. The optical system of claim 1 further comprising a wireless transceiver in communication with the digital delay generator that transmits the at least one output of the plurality of optical interferometers and the output of the excitation-emission device at the same rate as the data is received.

3. The optical system of claim 1 where the at least one of the optical interferometers and the excitation-emission device are further synchronized by an optical shutter.

4. The optical system of claim 1 where the at least one of the optical interferometers and the excitation-emission device are further synchronized by a plurality of wavelength selective devices.

5. The optical system of claim 1 where the at least one of the optical interferometers and the excitation-emission device are further synchronized by a plurality of charge coupled device sensors.

6. The optical system of claim 1 where the digital delay generator is in communication with a non-volatile memory that stores programmable sequences that synchronizes the at least one of the optical interferometers and the excitation-emission device to obtain a qualitative phase and emission data of the portion of the sample substantially simultaneously.

7. The optical system of claim 1 where the plurality of optical interferometers generates a plurality of interference phenomena that renders a plurality of images of the portion of the sample substantially simultaneously.

8. The optical system of claim 7 where the plurality of optical interferometers generates at least two images.

9. The optical system of claim 1 where the plurality of optical interferometers generates at least three images.

10. The optical system of claim 1 where the plurality of optical interferometers generates at least two images.

11. The optical system of claim 1 where the plurality of optical interferometers comprises a plurality of holographic devices that generate more than one hologram that is written to a memory through a single image.

12. The optical system of claim 11 where each of the more than one holograms are separated by a plurality of spatial frequencies.

13. The optical system of claim 1 where the at least one output of the plurality of optical interferometers and the output of the excitation-emission are captured by one of a monochrome charge coupled device and a red, green, blue (RGB) charge-coupled device, respectively.

14. The optical system of claim 1 further comprising a motorized filter wheel disposed between a filter cube of the excitation-emission device and a charge coupled device camera.

15. The optical system of claim 14 further comprising a rotary encoder that generates positional feedback to the digital delay generator.

16. The optical system of claim 1 further comprising a publicly accessible network that enables remote users to access real-time magnified images of the sample generated from the integration of the at least one output of plurality of optical interferometers and the output of the excitation emission device from a remote site.

17. The optical system of claim 1 further comprising a privately accessible network that enables remote users to access real-time magnified images of the sample generated from the integration of the at least one output of the plurality of optical interferometers and the output of the excitation-emission device from a remote site.

18. The optical system of claim 1 further comprising a graphical user interface programmed to allow an operator to enter point of interest identifiers that record characteristics associated with the image.

19. The optical system of claim 1, wherein the plurality of optical interferometers is further configured to generate an angle between the first combined optical wave and the second optical wave that generates a frequency modulation in the interference phenomena between the first combined optical wave and the second combined optical wave.

20. The optical system of claim 19, wherein the plurality of optical interferometers is further configured to provide a tilt to a combination of a reflecting surface and a beam splitter in a path of one of the first combined optical wave and the second combined optical wave, the tilt being provided to generate the angle between the first combined optical wave and the second optical combined wave.

21. An optical system comprising:
a plurality of optical interferometers configured to:
  split light emitted from a plurality of light sources into first and second optical waves;
  combine the first optical waves into a first combined optical wave that is transmitted through a sample; and
  combine the second optical waves into a second combined optical wave that serves as a reference wave;
  generate an interference phenomena between the first combined optical wave that is transmitted through the sample and the second combined optical wave to measure a plurality of distances, a plurality of thicknesses, and a plurality of indices of refraction of at least a portion of the sample,
an objective an objective in optical communication with the sample, the objective configured to:
  receive the first combined optical wave after the first combined optical wave is transmitted through the sample;
  transmit an electromagnetic excitation to the sample, the electromagnetic excitation being transmitted to the sample for generation of emissions by the sample when the sample is subjected to the electromagnetic excitation; and
  receive the emissions generated by the sample;
an excitation-emission device configured to transmit the electromagnetic excitation to the objective;
an electromagnetic detector that receives at least one output of the plurality of optical interferometers and an output of the excitation-emission device to render a magnified image of the at least a portion of the sample;
a digital delay generator that synchronizes the plurality of optical interferometers and excitation-emission device to operate in unison to generate a noninvasive depth of field of the portion of the sample in real-time;
a display that renders a magnified image of the at least portion of the sample in real time, where the electromagnetic detector comprises a monochrome charge coupled device that stores a portion of the at least one output of the plurality of optical interferometers; and
a red, green, blue (RGB) charge coupled device camera that stores a portion of the output of the excitation-emission device in a memory.

* * * * *

UNITED STATES PATENT AND TRADEMARK OFFICE
CERTIFICATE OF CORRECTION

PATENT NO. : 8,264,694 B2  
APPLICATION NO. : 12/405089  
DATED : September 11, 2012  
INVENTOR(S) : Christopher J. Mann et al.

Page 1 of 1

It is certified that error appears in the above-identified patent and that said Letters Patent is hereby corrected as shown below:

On the Title Page

In the left column, after item (65), insert a new item as follows.

-- Related U.S. Application Data
This application is related to Application No. 12/405,063, filed on March 16, 2009; and Application No. 12/381,758, filed on March 16, 2009.--

In the Claims

In column 9, claim 1, line 24, after "the at least" insert --a--.

In column 9, claim 2, line 30, after "at the same rate as" delete "the".

In column 10, claim 16, line 13, after "one output of" insert --the--.

In column 10, claim 20, line 38, replace "optical combined wave" with --combined optical wave--.

In column 10, claim 21, line 53, delete "an objective" (second occurrence).

In column 11, claim 21, line 7, after "of the at least" insert --a--.

In column 12, claim 21, line 4, after "(RGB)" replace "charge coupled" with --charge-coupled--.

Signed and Sealed this  
Seventeenth Day of September, 2013

Teresa Stanek Rea  
*Deputy Director of the United States Patent and Trademark Office*